United States Patent
Peng et al.

(10) Patent No.: US 12,421,180 B2
(45) Date of Patent: Sep. 23, 2025

(54) PROCESSES FOR PRODUCING Z-1,1,1,4,4,4-HEXAFLUOROBUT-2-ENE AND INTERMEDIATES FOR PRODUCING SAME

(71) Applicant: THE CHEMOURS COMPANY FC, LLC, Wilmington, DE (US)

(72) Inventors: Sheng Peng, Hockessin, DE (US); Allen Capron Sievert, Elkton, MD (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 556 days.

(21) Appl. No.: 17/601,515

(22) PCT Filed: Apr. 3, 2020

(86) PCT No.: PCT/US2020/026692
§ 371 (c)(1),
(2) Date: Oct. 5, 2021

(87) PCT Pub. No.: WO2020/206335
PCT Pub. Date: Oct. 8, 2020

(65) Prior Publication Data
US 2022/0194882 A1  Jun. 23, 2022

Related U.S. Application Data

(60) Provisional application No. 62/829,854, filed on Apr. 5, 2019.

(51) Int. Cl.
C07C 17/087 (2006.01)
C07C 17/04 (2006.01)
C07C 17/20 (2006.01)
C07C 17/25 (2006.01)
C07C 17/269 (2006.01)
C07C 17/354 (2006.01)

(52) U.S. Cl.
CPC ............ C07C 17/087 (2013.01); C07C 17/04 (2013.01); C07C 17/206 (2013.01); C07C 17/25 (2013.01); C07C 17/269 (2013.01); C07C 17/354 (2013.01)

(58) Field of Classification Search
CPC .................................................... C07C 17/269
See application file for complete search history.

(56) References Cited

U.S. PATENT DOCUMENTS

| | | | |
|---|---|---|---|
| 4,172,957 A * | 10/1979 | Correia | C07C 51/58 |
| | | | 562/602 |
| 5,315,047 A | 5/1994 | Lui et al. | |
| 2011/0288349 A1 * | 11/2011 | Poss | C07C 17/25 |
| | | | 570/156 |
| 2017/0015607 A1 * | 1/2017 | Baldychev | C07C 17/354 |
| 2019/0077733 A1 | 3/2019 | Peng | |

FOREIGN PATENT DOCUMENTS

| | | | | |
|---|---|---|---|---|
| CN | 103172489 A | * | 6/2013 | |
| WO | 2006069108 A1 | | 6/2006 | |
| WO | WO-2014052695 A1 | * | 4/2014 | C07C 17/25 |
| WO | 2015142981 A1 | | 9/2015 | |
| WO | 201951389 A1 | | 3/2019 | |

OTHER PUBLICATIONS

Machine translation of Patent No. CN103172489A, Jun. 26, 2013; pp. 1-8 (Year: 2013).*
International Search Report and Written Opinion Issued Jul. 24, 2020, 8 Pages.
Gokmen, et al., Synthesis of Tris(Arylthio)-1,3-Butadienes by Nucleophilic Vinylic Substitution of Polyhalogenated Nitrodienes and Structural Elucidation of the Products, Phosphorus, Sulfur, and Silicon and the Related Elements, 2015, pp. 93-102, vol. 190.

* cited by examiner

Primary Examiner — Medhanit W Bahta

(57) ABSTRACT

Processes for producing Z-1,1,1,4,4,4-hexafluorobut-2-ene and intermediates for producing same. A process for producing 2-chloro-1,1,1,4,4,4-hexafluorobutane comprises contacting 1,1,2,4,4-pentachlorobuta-1,3-diene with HF in the liquid phases. A process for producing E-1,1,1,4,4,4-hexafluorobut-2-ene comprises contacting 2-chloro-1,1,1,4,4,4-hexafluorobutane with base. A process for producing 2,3-dichloro-1,1,1,4,4,4-hexafluorobutane comprises contacting E-1,1,1,4,4,4-hexafluorobut-2-ene with a chlorine source. A process for producing 1,1,1,4,4,4-hexafluoro-2-butyne comprises contacting 2,3-dichloro-1,1,1,4,4,4-hexafluorobutane with a base. A process for producing Z-1,1,1,4,4,4-hexafluorobut-2-ene comprises contacting 1,1,1,4,4,4-hexafluoro-2-butyne with hydrogen and a catalyst.

13 Claims, No Drawings

PROCESSES FOR PRODUCING Z-1,1,1,4,4,4-HEXAFLUOROBUT-2-ENE AND INTERMEDIATES FOR PRODUCING SAME

CROSS REFERENCE TO RELATED APPLICATIONS

This application is a national filing under 35 U.S. C. 371 of International Application No. PCT/US2020/026692 filed Apr. 3, 2020, and claims the benefit of priority of U.S. Provisional Application No. 62/829,854 filed Apr. 5, 2019, the disclosures of which are incorporated herein by reference in its entirety.

TECHNICAL FIELD

The disclosure herein relates to a process for producing Z-1,1,1,4,4,4-hexafluoro-2-butene, and intermediates useful its production. The disclosure further provides processes for producing 2-chloro-1,1,1,4,4,4-hexafluorobutane, E-1,1,1,4,4,4-hexafluoro-2-butene, and 2,3-dichloro-1,1,1,4,4,4-hexafluorobutane.

BACKGROUND

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as refrigerants, cleaning agents, expansion agents for thermoplastic and thermoset foams, heat transfer media, gaseous dielectrics, aerosol propellants, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs). HFCs have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus, there is a need for manufacturing processes that provide intermediates useful to produce hydrofluoroolefins and hydrofluoroolefins that contain no chlorine. These materials have no ozone depletion potential and have low global warming potential.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

SUMMARY

The present disclosure provides a process for the production of hydrofluoroolefin Z-1,1,1,4,4,4-hexafluorobut-2-ene (Z-HFO-1336mzz, or Z-1336mzz). This process comprises (a) contacting 1,1,2,4,4-pentachlorobuta-1,3-diene with HF in the liquid phase in the presence of a fluorination catalyst to produce a product mixture comprising 2-chloro-1,1,1,4,4,4-hexafluorobutane; (b) contacting 2-chloro-1,1,1,4,4,4-hexafluorobutane with base to produce a product mixture comprising E-1,1,1,4,4,4-hexafluorobut-2-ene (E-HFO-1336mzz, or E-1336mzz); (c) contacting E-1,1,1,4,4,4-hexafluorobut-2-ene with a chlorine source to produce a product mixture comprising 2,3-dichloro-1,1,1,4,4,4-hexafluorobutane; (d) contacting 2,3-dichloro-1,1,1,4,4,4-hexafluorobutane with base to produce a product mixture comprising 1,1,1,4,4,4-hexafluoro-2-butyne; and (e) contacting 1,1,1,4,4,4-hexafluoro-2-butyne with hydrogen in the presence of a catalyst to produce a product mixture comprising Z-1,1,1,4,4,4-hexafluoro-2-butene.

In some embodiments, 1,1,2,4,4-pentachlorobuta-1,3-diene (HCC-2320az, 2320az) is produced according to a process comprising dimerization of trichloroethylene (TCE). A process to produce 2320az comprises contacting TCE in the presence of a catalyst to produce a product mixture comprising 2320az.

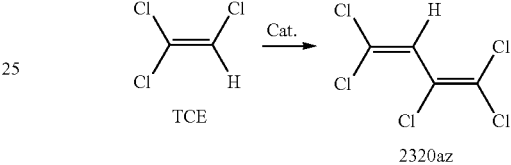

In some embodiments, the dimerization of TCE is performed in the presence of pentachloroethane ($CCl_3CHCl_2$, HCC-120), which accelerates the dimerization process.

In certain embodiments, 2320az is produced with a selectivity at least 80%; in some embodiments, selectivity is greater than 90% or greater than 95% or greater than 99% or greater than 99.5%. In certain embodiments, 2320az is recovered from the product mixture. In some embodiments, unreacted TCE is recovered and recycled. In some embodiments pentachloroethane is recovered and recycled.

In some embodiments, 2-chloro-1,1,1,4,4,4-hexafluorobutane (HCFC-346mdf or 346mdf) is produced by contacting 1,1,2,4,4-pentachlorobuta-1,3-diene (HCC-2320az, or 2320az) with hydrogen fluoride (HF) in the liquid phase in the presence of a catalyst to product mixture comprising 346mdf.

In the process of this disclosure, 346mdf is contacted with base to produce E-1,1,1,4,4,4-hexafluoro-2-butene (E-1336mzz).

In some embodiments, 2,3-dichloro-1,1,1,4,4,4-hexafluorobutane ($CF_3CHClCHClCF_3$) (HCFC-336mdd, 336mdd) is produced by contacting E-1336mzz with chlorine ($Cl_2$) in the liquid or vapor phase optionally in the presence of a catalyst or with photoinitiation to product mixture comprising 336mdd.

In some embodiments, 336mdd is used in a process to produce 1,1,1,4,4,4-hexafluoro-2-butyne, which process comprises contacting 336mdd with base. In some embodiments, 1,1,1,4,4,4-hexafluoro-2-butyne is recovered and then reacted with hydrogen to form Z-1,1,1,4,4,4-hexafluoro-2-butene.

The present disclosure further provides compositions produced according to the processes disclosed herein.

DETAILED DESCRIPTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

By "recovering" it is meant to sufficiently isolate the desired product to make it available for its intended use, either as a starting material for a subsequent reaction step or, in the case of recovering E-1,1,1,4,4,4-hexafluoro-2-butene or Z-1,1,1,4,4,4-hexafluoro-2-butene, useful, for example, as a refrigerant or foam expansion agent or solvent or fire extinguishant or electronic gas.

The details of the recovery step will depend on the compatibility of the product mixture with the reaction conditions of the subsequent reaction step. For example, if the product is produced in a reaction medium that is different from or incompatible with a subsequent reaction step, then the recovery step may include separation of the desired product from the product mixture including the reaction medium. This separation may occur simultaneously with the contacting step when the desired product is volatile under the reaction conditions. The volatilization of the desired product can constitute the isolation and thereby the recovery of the desired product. If the vapors include other materials intended for separation from the desired product, the desired product may be separated, by selective distillation, for example.

The steps for recovering the desired product from the product mixture, preferably comprise separating the desired product from catalyst or other component(s) of the product mixture used to produce the desired product or produced in the process.

The present disclosure provides, inter alia, processes to produce E-1336mzz and Z-1336mzz. A starting material may comprise 1,1,2,4,4-pentachlorobuta-1,3-diene, which may be produced from trichloroethylene, one process is as set forth herein.

Production of 1,1,2,4,4-pentachlorobuta-1,3-diene (2320az)

1,1,2,4,4-pentachlorobuta-1,3-diene (HCC-2320az, or 2320az) may be produced in accordance with this disclosure by dimerization of trichloroethylene (TCE). In some embodiments, there is provided a process to produce a product mixture comprising 2320az, which process comprises contacting TCE with a dimerization catalyst at an elevated temperature.

In some embodiments, the dimerization catalyst comprises iron. An iron dimerization catalyst may comprise metallic iron from any source (including a combination of sources) and may be or comprise iron powder, iron wire, iron screen or iron turnings. The iron catalyst may also comprise an iron salt such as ferric chloride or ferrous chloride ($FeCl_3$ or $FeCl_2$, respectively).

In some embodiments, the dimerization catalyst comprises copper. A copper dimerization catalyst may comprise metallic copper from any source (including a combination of sources) and may be or comprise copper powder or copper wire, for example. The copper catalyst may also comprise a cuprous or a cupric salt such as cuprous chloride or cupric chloride ($CuCl$ or $CuCl_2$, respectively).

The process is preferably performed in an anhydrous environment. For example, when ferric chloride is used, the ferric chloride is preferably anhydrous.

In some embodiments, the dimerization catalyst has a particular concentration with respect to moles of TCE reactant used. As such, in some embodiments wherein the catalyst comprises a metallic iron catalyst, a ratio of weight of Fe wire (or Fe powder) catalyst to TCE is from about 0.0001 to about 1. In other embodiments, the weight ratio of iron catalyst to TCE is from about 0.01 to about 1.

In some embodiments, the dimerization catalyst comprises ferric chloride and the weight ratio of ferric chloride to TCE is from about 0.00001 to about 1. For example, the weight ratio of ferric chloride to TCE is from about 0.00001 to about 0.002, while in another example, the weight ratio is from about 0.00005 to about 0.001. In yet another example, a weight ratio of ferric chloride to TCE is from about 0.0001 to about 1, while in a further example, the ratio of ferric chloride to TCE is from about 0.00015 to about 1.

In some embodiments, trichloroethylene is contacted with a dimerization catalyst and pentachloroethane. Pentachloroethane (HCC-120) accelerates the reaction to produce the product mixture comprising 2320az. In certain embodiments, a weight ratio of HCC-120 to TCE is from about 0.001 to about 1. In other embodiments, the weight ratio of HCC-120 to TCE is from about 0.005 to about 1.

The dimerization of TCE is performed at an elevated temperature, for example at a temperature in the range of about 210 to about 235° C. The temperature may be greater than 200° C. The temperature may be less than 245° C.

Pressure is typically autogenous.

Contact (residence) time is typically about 0.5 to 10 hours.

In some embodiments, conversion of TCE is at least 15% or at least 30%, or at least 50%. In some embodiments, selectivity to 2320az is at least 80%, or at least 85%, or at least 90%.

Byproducts in the dimerization reaction may include tetrachloroethane isomers, tetrachlorobutadiene isomers, hexachlorobutene isomers, trichloroethylene oligomers. The product mixture comprising 2320az may further comprise E-1,1,2,3,4-pentachloro-1,3-butadiene or Z-1,1,2,3,4-pentachloro-1,3-butadiene. Thus, in one embodiment there is a composition comprising 1,1,2,4,4-pentachlorobuta-1,3-diene, E-1,1,2,3,4-pentachlorobuta-1,3-diene, and Z-1,1,2,3,4-pentachlorobuta-1,3-diene.

The process may further comprise recovering 2320az from the product mixture prior to use of the recovered 2320az as a starting material in a process to produce HCFC-346mdf, HFO-E-1336mzz, HCFC-336mdd, 1,1,1,4,4,4-hexafluoro-2-butyne and HFO-Z-1336mzz, for example, as set forth herein.

Processes for recovering 2320az from the product mixture may include one or any combination of purification techniques, such as distillation, that are known in the art. By "recovering" 2320az from the product mixture, a product comprising at least 95% or at least 97% or at least 99% 2320az is produced.

In certain embodiments, the process to produce 2320az may further comprise recovering trichloroethylene from the product mixture and recycling the recovered trichloroethylene to the dimerization process as set forth herein.

In certain embodiments, the process to produce 2320az may further comprise recovering hexachlorobutene isomers from the product mixture and recycling the recovered hexachlorobutene isomers to the dimerization process as set forth herein.

In certain embodiments, the process to produce 2320az may further comprise recovering pentachloroethane from the product mixture and recycling the recovered pentachloroethane to the dimerization process as set forth herein.

Other products, if present, such as E-1,1,2,3,4-pentachloro-1,3-butadiene and Z-1,1,2,3,4-pentachloro-1,3-butadiene may also be recovered.

Production of 2-chloro-1,1,1,4,4,4-hexafluorobutane (HCFC-346mdf)

According to the process provided herein, there is provided a process comprising contacting 1,1,2,4,4-pentachlorobuta-1,3-diene (2320az) with HF in the presence of a catalyst in the liquid phase to produce a product mixture comprising HCFC-346mdf (346mdf).

Fluorination catalysts which may be used in the liquid phase process of the invention include those derived from Lewis acid catalysts such as metal halides. The halide may be chosen from fluoride, chloride, and bromide, or combination thereof. The metal halide may be transition metal halide or other metal halide. Transition metal chlorides include halides of titanium, zirconium, hafnium, tantalum, niobium, tin, molybdenum, tungsten and antimony. Other suitable metal halide catalysts include boron trichloride, boron trifluoride, and arsenic trifluoride In some embodiments, the liquid phase fluorination may be conducted in a reaction zone comprising any reaction vessel of appropriate size for the scale for the reaction. In some embodiments, the reaction zone is a reaction vessel comprised of materials which are resistant to corrosion. In some embodiments, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, New York) under the trademark Monel®, or vessels having fluoropolymers linings. In other embodiments, the reaction vessel may be made of other materials of construction including stainless steels, in particular those of the austenitic type, and copper-clad steel.

The molar ratio of HF to 2320az in some embodiments is from about 1 to about 35. In other embodiments, the molar ratio of HF to 2320az is from about 1 to about 25.

In some embodiments, the fluorination process is performed in at an elevated temperature, for example at a temperature in the range of 50 to 160° C. In some embodiments, the temperature may be greater than 100° C. In other embodiments, the temperature may be less than 150° C.

In some embodiments, the fluorination process is performed at a pressure in the range of 0 to 600 psi (0 to 4.1 MPa).

In some embodiments, residence time for the fluorination process may be from about 1 to about 25 hours. In other embodiments, residence time for the fluorination process may be from about 2 to about 10 hours. In other embodiments, residence time for the fluorination process may be from 4 to about 6 hours.

In some embodiments, the product mixture comprising 346mdf may further comprise one or more of 1,2-dichloro-1,1,4,4,4-pentafluorobutane, Z-1,1,1,4,4,4-hexafluoro-2-chloro-2-butene, E-1,1,1,4,4,4-hexafluoro-2-butene, and 1,1-dichloro-2,2,4,4,4-pentafluorobutane. In one embodiment, there is a composition comprising 2-chloro-1,1,1,4,4,4-hexafluorobutane (346mdf), 1,2-dichloro-1,1,4,4,4-pentafluorobutane (345mfd), Z-1,1,1,4,4,4-hexafluoro-2-chloro-2-butene (Z-1326mxz), E-1,1,1,4,4,4-hexafluoro-2-butene (E-1336mzz), and 1,1-dichloro-2,2,4,4,4-pentafluorobutane (345mfc).

In some embodiments, the product mixture is a composition comprising 346mdf comprises 1,1,1,4,4,4-hexafluorobutane (356mff), 1,1,1-trifluoro-2-trifluoromethylbutane (356mzz), Z-1,1,1,4,4,4-hexafluoro-2-chloro-2-butene (Z-1326mxz), E-1,1,1,4,4,4-hexafluoro-2-chloro-2-butene (E-1326mxz), Z-1,1,1,4,4,4-hexafluoro-2,3-dichlorobutene (Z-1316mxx), and E-1,1,1,4,4,4-hexafluoro-2,3-dichlorobutene (E-1316mxx). In an embodiment, the product mixture comprising 346mdf comprises greater than 0 and less than 2 weight % each of 356mff and 356mmz and greater than 0 and less than 3 weight % of Z-1326mxz, Z-1316mxx and E-1316mxx, and greater than 0 and less than 5 weight % of E-1326mxz. This composition is useful for producing E-1,1,1,4,4,4-hexafluoro-2-butene (E-1336mzz) as set forth herein.

In some embodiments, 346mdf is produced with a selectivity of greater than 90%, 92%, 94%, 95%, 96%, 97%, 98%, or 99%, with respect to other products.

The process may further comprise recovering 346mdf from the product mixture comprising 346mdf. Processes for recovering 346mdf include one or any combination of purification techniques, such as distillation, that are known in the art. By "recovering" 346mdf from the product mixture, a product comprising 346mdf comprising at least 98.5% or at least 99 or at least 99.5% 346mdf is produced.

In certain embodiments, the process to produce 346mdf may further comprise recovering 2320az from the product mixture and recycling the recovered 2320az to the fluorination process as set forth herein.

In some embodiments, the process for producing 346mdf as disclosed herein comprises (a') contacting trichloroethylene in the presence of a dimerization catalyst to produce a product mixture comprising 2320az; (a) contacting 2320az produced in step (a') with hydrogen fluoride in the liquid phase in the presence of a fluorination catalyst to produce a product mixture comprising 346mdf. Optionally, the 2320az is recovered after step (a') and prior to step (a).

In some embodiments, the process for producing 346mdf as disclosed herein comprises (a') contacting trichloroethylene in the presence of a dimerization catalyst and pentachloroethane to produce a product mixture comprising 2320az; (a) contacting 2320az produced in step (a') with hydrogen fluoride in the liquid phase in the presence of a fluorination catalyst to produce a product mixture comprising 346mdf. Optionally, the 2320az is recovered after step (a') and prior to step (a).

Variations on the elements of the process in steps (a') and (a) are disclosed herein above. The purity of 2320az is typically at least 97% before proceeding to step (a).

Production of (E)-1,1,1,4,4,4-hexafluorobut-2-ene (E-1336mzz)

There is further provided a process herein comprising contacting 346mdf with base to form a product mixture comprising E-1336mzz. Base is added in an effective amount to convert 346mdf to E-1336mzz.

In some embodiments, the base is chosen from lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide. In some embodiments, the base is potassium hydroxide. In some embodiments, the base is sodium hydroxide. In some embodiments, the base is in an aqueous solution. In some embodiments, the concentration of base in the aqueous solution is from about 4M to about 12 M.

In some embodiments, the process is performed in the presence of a phase transfer catalyst. In some embodiments, the phase transfer catalyst is chosen from quaternary ammonium salt, heterocyclic ammonium salt, organic phosphonium salt, and nonionic compound. In some embodiments, the phase transfer catalyst is selected from the group consisting of benzyltrimethylammonium chloride, benzyltriethylammonium chloride, methyltricaprylammonium chloride, methyltributylammonium chloride, methyltrioctylammonium chloride, dimethyldiphenylphosphonium iodide, methyltriphenoxyphosphonium iodide, tetrabutylphosphonium bromide, tetrabutylphosphonium chloride, hexadecyltributylphosphonium bromide, and DL-α-tocopherol methoxypolyethylene glycol succinate. In some embodiments, the phase transfer catalyst is methyltrioctylammonium chloride.

In some embodiments, the base is sodium hydroxide and the phase transfer catalyst is methyltrioctylammonium chloride.

In some embodiments, the product mixture further comprises one or more of hexafluoroisobutylene (1336mt), 1,1,1,4,4,4-hexafluorobutane (356mff), E-1-chloro-1,1,4,4,4-pentafluorobut-2-ene (13351zz), and Z—$CF_3CH=CHCF_3$. In some embodiments, E-$CF_3CH=CHCF_3$ is produced in a yield of about 95% or greater. In some embodiments, E-$CF_3CH=CHCF_3$ is produced with a selectivity of about 99 mol % or greater with respect to other components of the mixture.

In an embodiment, the product mixture is a composition comprising E-1336mzz and greater than 0 and less than 1 weight % each of Z-1336mzz and 1,1,1,4,4,4-hexafluorobutane (356mff), and greater than 0 and less than 0.5 weight % of 1,1,1-trifluoro-2-trifluoromethylbutene (1336mt, $CF_3(CF_3)C=CH_2$), and greater than 0 and less than 0.2 weight % of 1-chloro-1,1,4,4,4-pentafluorobut-2-ene (1335lzz, $CF_2ClCH=CHCF_3$).

In an embodiment, the product mixture is a composition comprising E-1336mzz and greater than 0 and less than 1 weight % total of Z- and E-1,1,2,4,4,4-hexafluorobutene (Z- and E-1336mzy, $CF_2HCF=CHCF_3$), and greater than 0 and less than 0.5 weight % total of Z- and E-1,1,1,4,4,4-hexafluoro-2-chloro-2-butene (Z- and E-1326mxz), and greater than 0 and less than 0.2 weight % total of Z- and E-1,1,1,4,4-pentafluoro-2-chlorobutene (Z- and E-1335mxz, $CF_2HCH=CClCF_3$), and greater than 0 and less than 0.2 weight % total of Z- and E-1,1,1,4,4-pentafluoro-3-chlorobutene (Z- and E-1335mzx, $CF_2HCCl=CHCF_3$).

In an embodiment, the product mixture is a composition comprising E-1336mzz and greater than 0 and less than 1 weight % each of 1,1,1,4,4,4-hexafluorobutane (356mff, $CF_3CH_2CH_2CF_3$), 1,1,1-trifluoro-2-trifluoromethylbutane (356mmz, $(CF_3)_2CHCH_3$) and 1,1,4,4,4-pentafluoro-2-methylbut-1-ene (1345 cm, $CF_3C(CH_3)=CF_2$), and greater than 0 and less than 0.1 weight % total of Z- and E-1,1,1,4,4,4-hexafluoro-2-chloro-2-butene (Z- and E-1326mxz), and greater than 0 and less than 0.1 weight % total of Z- and E-1,1,1,4,4,4-hexafluoro-2,3-dichlorobutene (Z- and E-1316mxx, $CF_3CCl=CClCF_3$).

In some embodiments of the process provided herein, E-1336mzz is recovered from the product mixture.

Production of HCFC-336mdd

The reaction of E-1336mzz with a chlorine source to produce a product mixture comprising 2,3-dichloro-1,1,1,4,4,4-hexafluorobutane ($CF_3CHClCHClCF_3$, HCFC-336mdd) is a chlorination process in which a chlorine source and E-1336mzz are reacted to produce a product mixture comprising the desired HCFC-336mdd product. The process may be performed in the liquid phase in a liquid medium or in the vapor phase, each preferably in the presence of a chlorination catalyst or with photoinitiation. An example of liquid medium is the E-1336mzz reactant itself.

Photoinitiation is performed in a suitable photoinitiation apparatus which includes a light source, a source of chlorine ($Cl_2$) and E-1336mzz (the material to be chlorinated), as described, for example, in WO 2006/069108 A1.

Examples of suitable chlorination catalysts include Lewis acids, such as transition metal chlorides or aluminum chloride.

Catalysts for this chlorination process in the liquid phase may be chosen from ferric chloride, chromium chloride, alumina chloride, cupric chloride and combinations of two or more of these. Catalysts for this chlorination process in the vapor phase may be chosen from ferric chloride, chromium chloride, alumina chloride, cupric chloride and combinations of two or more of these supported on carbon.

The temperature and pressure conditions for the chlorination process are preferably selected to be effective to produce the HCFC-336mdd at high selectivity. In performing the process in the liquid phase such as supplied by E-1336mzz, the process is preferably performed in a closed pressurizable reactor within which the pressure is sufficient pressure to maintain the liquid state. The pressure within the reactor may be autogenous pressure or a high pressure. The desired product HCFC-336mdd may be recovered from the reactor when the process is carried out in a liquid medium by purging unreacted chlorine, distilling off unreacted E-1336mzz. The catalyst may be filtered off if present in sufficiently high concentration that catalyst precipitates from product mixture prior to or during or after distillation. Alternatively, the catalyst may remain in the distillation heel.

A tubular reactor may be used to carry out the process in the vapor state (phase). Chlorination catalyst, such as Lewis acid, may be positioned within the reactor for effective contact with E-1336mzz and chlorine source simultaneously fed into the reactor at a temperature and residence time effective to produce the desired HCFC-336mdd reaction product at the desired selectivity. The temperature of the chlorination process is maintained by applying heat to the reactor. Preferably the temperature of the process is in the range of 100° C. to 200° C. The pressure within the tubular reactor is preferably about 0.1 to 1 MPa. HCFC-336mdd may be recovered from the product mixture by distillation.

The chlorine source may be chosen from chlorine, N-chlorosuccinimide, t-butyl hypochlorite, oxalyl chloride, and sulfuryl chloride.

In an embodiment the reaction of E-1336mzz with a chlorine source is performed in the presence of a chlorination catalyst and the chlorine source is chlorine ($Cl_2$). In an embodiment the reaction of E-1336mzz with a chlorine source is performed in the absence of a chlorination catalyst and the chlorine source is chlorine ($Cl_2$).

In an embodiment the reaction of E-1336mzz with a chlorine source is performed with photoinitiation in the presence ultraviolet radiation and the chlorine source is chlorine.

In an embodiment the reaction of E-1336mzz with a chlorine source is performed in the absence of a chlorination catalyst and the chlorine source is N-chlorosuccinimide, t-butyl hypochlorite, oxalyl chloride, or sulfuryl chloride.

The process may further comprise recovering HCFC-336mdd from the product mixture to reduce the other components of the product mixture. Processes for recovering HCFC-336mdd may include one or any combination of purification techniques, such as distillation, that are known in the art. By "recovering" HCFC-336mdd from the product mixture, a product comprising at least 98.5% or at least 99 or at least 99.5% HCFC-336mdd is produced. In some embodiments, E-1336mzz may be recovered and recycled to the process or used for another purpose.

The chlorination of E-1336mzz preferably provides a selectivity to HCFC-336mdd of at least 85%, more preferably at least 90%, and most preferably, at least 95%, whether the reaction is carried out in the liquid phase or vapor phase.

The product mixture comprising 336mdd may further comprise one or more of HCFC-336mfa (2,2-dichloro-1,1,1,4,4,4-hexafluorobutane, $CF_3CCl_2CH_2CF_3$) and HCFC-326mda (2,3,3-trichloro-1,1,1,4,4,4-trifluoropropane, $CF_3CHClCCl_2CF_3$), which may be recovered from the product mixture. Alternatively, HCFC-336mfa and/or HCFC-326mda may be retained in the product mixture and carried forward to a subsequent step for producing hexafluoro-2-butyne.

In certain embodiments, the process to produce 336mdd may further comprise recovering unconverted E-1336mzz from the chlorination product mixture and recycling the recovered E-1336mzz to the chlorination process as set forth herein.

In some embodiments, unconverted E-1336mzz is recovered from the product mixture. In some embodiments, E-1336mzz may be and used for another purpose, such as a blowing agent or a heat transfer fluid.

Production of 1,1,1,4,4,4-hexafluoro-2-butyne

The present disclosure further provides a process comprising contacting HCFC-336mdd with base to produce a product mixture comprising 1,1,1,4,4,4-hexafluoro-2-butyne ($CF_3C{\equiv}CCF_3$) in a dehydrochlorination reaction. The base is preferably a basic aqueous medium. This reaction step is preferably performed in the presence of a catalyst. Preferably the basic aqueous medium comprises a solution of an alkali metal hydroxide or alkali metal halide salt or other base in water. Preferably the catalyst is a phase transfer catalyst. As used herein, phase transfer catalyst is intended to mean a substance that facilitates the transfer of ionic compounds between an organic phase and an aqueous phase. In this step, the organic phase comprises the HCFC-336mdd reactant, and the aqueous phase comprises the basic aqueous medium. The phase transfer catalyst facilitates the reaction of these dissimilar and incompatible components.

While various phase transfer catalysts may function in different ways, their mechanism of action is not determinative of their utility in the present invention provided that the phase transfer catalyst facilitates the dehydrochlorination reaction.

A preferred phase transfer catalyst is quaternary alkylammonium salt. In some embodiments, at least one alkyl group of the quaternary alkylammonium salt contains at least 8 carbons. An example of quaternary alkylammonium salt wherein three alkyl groups contain at least 8 carbon atoms includes trioctylmethylammonium chloride. Aliquat® 336 is a commercially available phase transfer catalyst which contains trioctylmethylammonium chloride. An example of quaternary alkylammonium salt wherein four alkyl groups contain at least 8 carbon atoms includes tetraoctylammonium salt. The anions of such salts may be halides such as chloride or bromide, hydrogen sulfate, or any other commonly used anion. Specific quaternary alkylammonium salts include tetraoctylammonium chloride, tetraoctylammonium hydrogen sulfate, tetraoctylammonium bromide, methytrioctylammonium chloride, methyltrioctylammonium bromide, tetradecylammonium chloride, tetradecylammonium bromide, and tetradodecylammonium chloride. According to such embodiments, the phase transfer catalyst and reaction conditions are effective to achieve conversion of HCFC-336mdd, preferably at least 50% per hour.

In other embodiments, the alkyl groups of the quaternary alkylammonium salt contain from 4 to 10 carbon atoms and a non-ionic surfactant is present in the aqueous basic medium. According to such embodiments, the phase transfer catalyst and reaction conditions are effective to achieve conversion of HCFC-336mdd preferably at least 20% per hour. The anions of quaternary alkylammonium salt wherein the alkyl group contains 4 to 10 carbon atoms may be halides such as chloride or bromide, hydrogen sulfate, or any other commonly used anion. Quaternary alkylammonium salts mentioned above may be used in this embodiment provided their alkyl groups contain 4 to 10 carbon atoms. Specific additional salts include tetrabutylammonium chloride, tetrabutylammonium bromide, and tetrabutylammonium hydrogen sulfate.

Preferred non-ionic surfactants include ethoxylated nonylphenol or an ethoxylated $C_{12}$-$C_{15}$ linear aliphatic alcohol. Non-ionic surfactants include Bio-Soft® N25-9 and Makon® 10 useful in the present invention are obtainable from Stepan Company, Northfield, IL.

In some embodiments, the quaternary alkylammonium salt is added in an amount of from 0.5 mole percent to 2 mole percent of the HCFC-336mdd. In other embodiments, the quaternary alkylammonium salt is added in an amount of from 1 mole percent to 2 mole percent of the HCFC-336mdd. In yet other embodiments, the quaternary alkylammonium salts is added in an amount of from 1 mole percent to 1.5 mole percent of the HCFC-336mdd. In some embodiments, the quaternary alkylammonium salt is added in an amount of from 1 mole percent to 1.5 mole percent of the HCFC-336mdd and the weight of non-ionic surfactant added is from 1 to 2 times the weight of the quaternary alkylammonium salt. These amounts apply to each of the above-mentioned embodiments of the quaternary alkylammonium salt used.

In some embodiments, the reaction is preferably conducted at a temperature of from about 60 to 90° C., most preferably at 70° C.

A basic aqueous medium is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid in the basic aqueous solution is at least 90% water. In some embodiments the water is tap water; in other embodiments the water is deionized or distilled.

The base is chosen from hydroxide, oxide, carbonate, or phosphate salts of alkali, alkaline earth metals and mixtures thereof. In some embodiments, the base is chosen from lithium hydroxide, sodium hydroxide, potassium hydroxide, calcium hydroxide, magnesium oxide, calcium oxide, sodium carbonate, trisodium phosphate, disodium hydrogenphosphate, sodium dihydrogen phosphate, tripotassium phosphate, dipotassium hydrogenphosphate, potassium dihydrogen phosphate, and mixtures thereof.

These embodiments of basic aqueous medium and bases apply to all of the phase transition catalysts, amounts, and reaction conditions mentioned above. The selectivity to the formation of 1,1,1,4,4,4-hexafluoro-2-butyne is preferably at least 85%.

In some embodiments, the dehydrochlorination reaction of 336mdd to 1,1,1,4,4,4-hexafluoro-2-butyne is performed in the presence of an alkali metal halide salt. The alkali metal may be sodium or potassium. The halide may be chloride or bromide. A preferred alkali metal halide salt is sodium chloride. Without wishing to be bound by any particular theory, it is believed that the alkali metal halide salt stabilizes the phase transfer catalyst. Although the dehydrochlorination reaction itself produces alkali metal chloride, and in particular sodium chloride if sodium hydroxide is used as the base, addition of extra sodium chloride provides a further effect of increasing the yield of 1,1,1,4,4,4-hexafluoro-2-butyne. In some embodiments, the alkali metal halide is added at from about 25 to about 100 equivalents per mole of phase transfer catalyst. In other embodiments, the alkali metal halide is added at from about 30 to about 75 equivalents per mole of phase transfer catalyst. In yet other embodiments, the alkali metal halide is added at from about 40 to about 60 equivalents per mole of phase transfer catalyst. These amounts apply to each of the quaternary alkylammonium salts mentioned above.

The product 1,1,1,4,4,4-hexafluoro-2-butyne (boiling point −25° C.) may be recovered from the product mixture by distillation, wherein the butyne vaporizes from the aqueous medium and can then be condensed. In addition, the product mixture may also contain 1,1,1,4,4,4-hexafluoro-2-chloro-2-butene (HCFO-1326, Z-isomer, E-isomer, or a mixture thereof), which may be separated from the product mixture and recycled to the process step comprising contacting HCFC-336mdd with base to produce a product mixture comprising $CF_3C\equiv CCF_3$ in a dehydrochlorination reaction.

Production of Z-1,1,1,4,4,4-hexafluoro-2-butene

The present disclosure further provides a hydrogenation process comprising contacting 1,1,1,4,4,4-hexafluoro-2-butyne with hydrogen to produce a product mixture comprising Z-1,1,1,4,4,4-hexafluoro-2-butene (Z-1336mzz). This process is preferably performed in the presence of an alkyne-to-alkene catalyst.

In some embodiments the hydrogenation of 1,1,1,4,4,4-hexafluoro-2-butyne is performed as a batch process in the liquid phase.

In some embodiments the hydrogenation of 1,1,1,4,4,4-hexafluoro-2-butyne is performed as a continuous process in the vapor phase.

In some embodiments, an alkyne-to-alkene catalyst is a palladium catalyst, such as palladium dispersed on aluminum oxide or titanium silicate, doped with silver and/or a lanthanide. The loading of palladium dispersed on the aluminum oxide or titanium silicate is relatively low. In some embodiments, the palladium loading is from about 100 ppm to about 5000 ppm. In other embodiments, the palladium loading is from about 200 ppm to about 5000 ppm. In some embodiments, the palladium catalyst is doped with at least one of silver, cerium or lanthanum. In some embodiments, the mole ratio of cerium or lanthanum to palladium is from about 2:1 to about 3:1. In some embodiments the mole ratio of silver to palladium is about 0.5:1.0.

Other embodiments of alkyne-to-alkene catalyst is Lindlar catalyst, which is a heterogeneous palladium catalyst on a calcium carbonate support, which has been deactivated or conditioned with a lead compound. The lead compound may be lead acetate, lead oxide, or any other suitable lead compound. In some embodiments, the catalyst is produced by reduction of a palladium salt in the presence of a slurry of calcium carbonate, followed by the addition of the lead compound. In some embodiments, the palladium salt in palladium chloride.

In other embodiments, the Lindlar catalyst is further deactivated or conditioned with quinoline. The amount of palladium on the support is typically about 5% by weight but may be any catalytically effective amount. In other embodiments, the amount of palladium on the support in the Lindlar catalyst is greater than 5% by weight. In yet other embodiments, the amount of palladium on the support may be from about 5% by weight to about 1% by weight.

In some embodiments, the amount of the catalyst used is from about 0.5% by weight to about 4% by weight of the amount of the 1,1,1,4,4,4-hexafluoro-2-butyne. In other embodiments, the amount of the catalyst used is from about 1% by weight to about 3% by weight of the amount of the butyne. In yet other embodiments, the amount of the catalyst used is from about 1% to about 2% by weight of the amount of the butyne.

In some embodiments, this reaction step is a batch reaction and is performed in the presence of a solvent. In one such embodiment, the solvent is an alcohol. Typical alcohol solvents include ethanol, i-propanol and n-propanol. In other embodiments, the solvent is a fluorocarbon or hydrofluorocarbon. Typical fluorocarbons or hydrofluorocarbons include 1,1,1,2,2,3,4,5,5,5-decafluoropentane and 1,1,2,2,3,3,4-heptafluorocyclopentane.

In some embodiments, reaction of the 1,1,1,4,4,4-hexafluoro-2-butyne with hydrogen is preferably performed with addition of hydrogen in portions, with increases in the pressure of the vessel of no more than about 100 psi (0.69 MPa) with each addition. In other embodiments, the addition of hydrogen is controlled so that the pressure in the vessel increases no more than about 50 psi (0.35 MPa) with each addition. In some embodiments, after enough hydrogen has been consumed in the hydrogenation reaction to convert at least 50% of the butyne to Z-1336mzz, hydrogen may be added in larger increments for the remainder of the reaction. In other embodiments, after enough hydrogen has been consumed in the hydrogenation reaction to convert at least 60% of the butyne to the desired butene, hydrogen may be added in larger increments for the remainder of the reaction. In yet other embodiments, after enough hydrogen has been consumed in the hydrogenation reaction to convert at least 70% of the butyne to desired butene, hydrogen may be added in larger increments for the remainder of the reaction. In some embodiments, the larger increments of hydrogen addition may be 300 psi (2.07 MPa). In other embodiments, the larger increments of hydrogen addition may be 400 psi (2.76 MPa).

In some embodiments, the molar ratio is about 1 mole of hydrogen to about 1 mole of 1,1,1,4,4,4-hexafluoro-2-butyne. In other embodiments, the molar ratio is from about 0.9 mole to about 1.3 mole, hydrogen to butyne. In yet other embodiments, the amount of hydrogen added is from about 0.95 mole of hydrogen to about 1.1 moles of butyne. In yet other embodiments, the amount of hydrogen added is from about 0.95 moles of hydrogen to about 1.03 moles of butyne.

In some embodiments, the hydrogenation is performed at ambient temperature (15° C. to 25° C.). In other embodiments, the hydrogenation is performed at above ambient temperature. In yet other embodiments, the hydrogenation is performed at below ambient temperature. In yet other embodiments, the hydrogenation is performed at a temperature of below about 0° C.

In an embodiment of a continuous process, a mixture of 1,1,1,4,4,4-hexafluoro-2-butyne and hydrogen is passed through a reaction zone containing the catalyst. A reaction vessel, e.g., a metal tube, may be used, packed with the catalyst to form the reaction zone. In some embodiments, the molar ratio of hydrogen to the butyne is about 1:1. In other embodiments of a continuous process, the molar ratio of hydrogen to the butyne is less than 1:1. In yet other embodiments, the molar ratio of hydrogen to the butyne is about 0.67:1.0.

In some embodiments of a continuous process, the reaction zone is maintained at ambient temperature. In other embodiments of a continuous process, the reaction zone is maintained at a temperature of 30° C. In yet other embodiments of a continuous process, the reaction zone is maintained at a temperature of about 40° C.

In some embodiments of a continuous process, the flow rate of 1,1,1,4,4,4-hexafluoro-2-butyne and hydrogen is maintained so as to provide a residence time in the reaction zone of about 30 seconds. In other embodiments of a continuous process, the flow rate of the butyne and hydrogen is maintained so as to provide a residence time in the reaction zone of about 15 seconds. In yet other embodiments of a continuous process, the flow rate of butyne and hydrogen is maintained so as to provide a residence time in the reaction zone of about 7 seconds.

It will be understood, that residence time in the reaction zone is reduced by increasing the flow rate of 1,1,1,4,4,4-hexafluoro-2-butyne and hydrogen into the reaction zone. As the flow rate is increased this will increase the amount of butyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

The conditions of the contacting step, including the choice of catalyst, are preferably selected to produce Z-1336mzz at a selectivity of at least 85%, more preferably at least 90%, and most preferably at least 95%.

In some embodiments, upon completion of a batch-wise or continuous hydrogenation process, the Z-1336mzz may be recovered through any conventional process, including for example, fractional distillation. Unconverted hexafluoro-2-butyne may be recovered and recycled to the hydrogenation process. In other embodiments, upon completion of a batch-wise or continuous hydrogenation process, the Z-1336mzz is of sufficient purity to not require further purification steps.

EXAMPLES

Materials

Trichloroethylene, chlorine, ferric chloride, $TaCl_5$, pentachloroethane (HCC-120), tetra-n-butylammonium bromide (TBAB), trioctylmethylammonium chloride (Aliquat® 336), NaOH and Lindlar catalyst are available from Sigma Aldrich, St. Louis, MO Hydrogen fluoride was purchased from Synquest Labs, Inc., Alachua, FL. Makon® 10 non-ionic surfactant is available from Stepan Company, Northfield, IL.

GC analysis for Examples 1-4 was performed using Agilent® 5975GC, RESTEK Rtx-1 column.

Example 1: Preparation of 1,1,2,4,4-pentachlorobuta-1,3-diene (HCC-2320az)

Trichloroethylene (100 g, 0.76 mol) was added to a shaker tube containing 30 mg anhydrous $FeCl_3$. The reaction mixture was heated at 230° C. for 2 hrs. The reactor content was cooled to room temperature and analyzed by GC to determine the conversion and selectivity. Results are provided in Table 1.

Example 2: Preparation of 1,1,2,4,4-pentachlorobuta-1,3-diene (HCC-2320az)

Trichloroethylene (100 g, 0.76 mol) was added to a shaker tube containing 1 g iron wire. The reaction mixture was heated at 230° C. for 2 hrs. The reactor content was cooled to room temperature and analyzed by GC to determine the conversion and selectivity. Results are provided in Table 1.

Example 3: Preparation of 1,1,2,4,4-pentachlorobuta-1,3-diene (HCC-2320az)

Trichloroethylene (100 g, 0.76 mol) was added to a shaker tube containing 20 mg anhydrous $FeCl_3$ and 1 g HCC-120. The reaction mixture was heated at 230° C. for 2 hrs. The reactor content was cooled to room temperature and analyzed by GC to determine the conversion and selectivity. Results are provided in Table 1.

Example 4: Preparation of 1,1,2,4,4-pentachlorobuta-1,3-diene (HCC-2320az)

Trichloroethylene (100 g, 0.76 mol) was added to a shaker tube containing 1 g iron wire and 1 g HCC-120. The reaction mixture was heated at 230° C. for 2 hrs. The reactor content was cooled to room temperature and analyzed by GC to determine the conversion and selectivity. Results are provided in Table 1.

TABLE 1

| Trichloroethylene Dimerization to 2320az | | | |
|---|---|---|---|
| Example | Catalyst | Time (hours) | Conversion/ Selectivity (%) |
| 1 | $FeCl_3$ (30 mg) | 16 | 26.9/81.6 |
| 2 | Fe wire (1 g) | 8 | 28.0/86.7 |
| 3 | $FeCl_3$ (20 mg)/HCC-120 (1 g) | 2 | 35.4/84.3 |
| 4 | Fe wire (1 g)/HCC-120 (1 g) | 2 | 32.3/87.4 |

As can be seen from Table 1, the presence of HCC-120 increases conversion rate of trichloroethylene to 2320az when using $FeCl_3$ or Fe wire catalyst.

Example 5: Preparation of 2-chloro-1,1,1,4,4,4-hexafluorobutane (HCFC-346mdf)

TaCl$_5$ (12.5 g) was added to a 210 mL Hastelloy® C reactor, followed by HF (49 g). The reaction mixture was heated to 150° C. for 1 hour and cooled to 0° C. HCC-2320az (26 g) was added to the reactor and the reaction was heated back to 130° C. The reaction rate was indicated by pressure increase. The level-off pressure means the completion of the reaction. After aqueous work up and phase separation, the product mixture was analyzed by GC and showed 100% conversion of starting material, and 98% selectivity to product HCFC-346mdf.

Example 6: Preparation of E-CF$_3$CH═CHCF$_3$ (E-1336mzz)

An aqueous solution of NaOH (6 mL, 0.06 mol) was added to 346mdf (10 g, 0.05 mol) and water (6.8 mL) at room temperature (RT) in the presence of 0.27 g of methyltrioctylammonium chloride (Aliquat® 336). The reaction temperature was raised to 70° C. after the addition, and gas chromatography was used to monitor the reaction. After 2 hours, 7.2 g of product E-CF$_3$CH═CHCF$_3$ (E-1336mzz) was collected in a dry ice trap (E-1336mzz selectivity 99.4%, yield: 95.4%).

Example 7: Preparation of E-CF$_3$CH═CHCF$_3$ (E-1336mzz)

An aqueous solution of KOH (6 mL, 0.06 mol) was added to 346mdf (10 g, 0.05 mol) and water (6.8 mL) at room temperature (RT). The reaction temperature was raised to 70° C. after the addition, and gas chromatography was used to monitor the reaction. After 2 hours, 7.6 g of product E-1336mzz was collected in a dry ice trap (E-1336mzz selectivity 99.5%, yield: 96%).

The product composition is shown in Table 2, below, and contains greater than 99% E-1336mzz.

TABLE 2

| Product composition | |
|---|---|
| Products | % |
| E-1336 mzz (E—CF$_3$CH═CHCF$_3$) | >99 |
| Z-1336 mzz (Z—CF$_3$CH═CHCF$_3$) | <0.4 |
| 1336 mt (CF$_3$(CF$_3$)C═CH$_2$) | <0.2 |
| 356 mff (CF$_3$CH$_2$CH$_2$CF$_3$) | <0.4 |
| 1335 lzz (CF$_2$ClCH═CHCF$_3$) | Trace (<0.1) |

Comparative Example: Preparation of E-CF$_3$CH═CHCF$_3$ (E-1336mzz)

An aqueous solution of NaOH (6 mL, 0.06 mol) was added to 346mdf (10 g, 0.05 mol) and water (6.8 mL) at room temperature (RT). The reaction temperature was raised to 70° C. after the addition, and gas chromatography was used to monitor the reaction. After 2 hours, 0.1 g of product E-CF$_3$CH═CHCF$_3$ (E-1336mzz) was collected in a dry ice trap (yield: <1%).

Example 8: Liquid Phase Preparation of 2,3-dichloro-1,1,1,4,4,4-hexafluorobutane (HCFC-336mdd)

In this Example, E-1336mzz is catalytically and thermally chlorinated in the liquid phase to produce HCFC-336mdd. Lewis acid catalysts are used.

The liquid phase reaction was carried out in a Hast® C reactor. The liquid medium was E-1336mzz reactant. Catalyst when used was present in the liquid phase. The reactor content was transferred to a cylinder and analyzed by GC to determine the conversion and selectivity. The HCFC-336mdd was recovered from the reaction by purging unreacted chlorine, distilling off the unreacted E-1336mzz and filtering off the catalyst. Reaction conditions and results are given in Table 3.

TABLE 3

| Liquid Phase Thermal Chlorination of E-1336 mzz | | | | |
|---|---|---|---|---|
| Examples | Catalyst | T (° C.) | Time (hr) | Conversion/ Selectivity (%) |
| 8-1 | FeCl$_3$ | 150 | 0.5 | 60/100 |
| 8-2 | FeCl$_3$ | 130 | 2 | 12/>99 |
| 8-3 | FeCl$_3$ | 100 | 1 | 0/0 |
| 8-4 | CrCl$_3$ | 150 | 1 | 60/87.3 |
| 8-5 | AlCl$_3$ | 150 | 2 | 69/97.6 |
| 8-6 | CuCl$_2$ | 150 | 2 | 60/98 |
| 8-7 | None | 120 | 2 | 0/0 |
| 8-8 | None | 180 | 2 | 63/40 |

For each of Examples 8-1 to 8-6, E-1336mzz (20 g, 0.122 mole) and chlorine (8.65 g, 0.122 mole) were heated to the recited temperature in the presence of FeCl$_3$, CrCl$_3$, AlCl$_3$ or CuCl$_2$ catalyst (0.4 g, 0.0025 mole) in the Hast® C reactor for the recited time. Recited temperatures and recited times are provided in Table 3.

For Examples 8-7 and 8-8, the E-1336mzz (20 g, 0.122 mole) and chlorine (8.65 g, 0.122 mole) were heated to the temperatures recited in Table 3 in a 210 mL Hastelloy® C reactor to the temperatures recited in Table 3 for 2 hours. No catalyst was present.

Comparison of the results for Examples 8-1 to 8-8 indicates the preference for the reaction being carried out in the presence of catalyst as well as at a temperature of at least 130° C. or at least 150° C.

Example 9: Vapor Phase Preparation of 2,3-dichloro-1,1,1,4,4,4-hexafluorobutane (HCFC-336mdd)

The procedure for the vapor phase reaction was as follows: an Inconel® tube (0.5 inch OD, 15 inch length, 0.34 in wall thickness) was filled with 2 cc (1.10 gm) of ferric chloride on acid washed Takeda® carbon. The reactor was heated in a Lindberg furnace to 125° C. and CF$_3$CH═CHCF$_3$ (E-1336mzz) was fed at 2.42-4.83 ml/hour and chlorine gas at 6.2-13.0 sccm (standard cubic centimeters per minute) through a vaporizer controlled at 80° C. Over the course of the run, the temperature was raised to 175° C. All of the experiments below were carried out at 49-51 psig (0.34-0.35 MPa). The effluent of the reactor was analyzed online using an Agilent® 6890 GC/5973 MS and a Restek® PC2618 5% Krytox® CBK-D/60/80 6 meter×2 mm ID ⅛" OD packed column purged with helium at 30 sccm. The HCFC-336mdd was recovered by distillation.

The data is shown in Table 4. Samples are taken in hourly intervals.

TABLE 4

Vapor phase Chlorination of E-1336mzz

| Mole Percents | | | | | | | | | | | | |
|---|---|---|---|---|---|---|---|---|---|---|---|---|
| Unknowns % | 236fa % | 1336 % | 133a % | 123 % | 336 % | Furnace ° C. | Pressure (MPa) | Pump ml/hr | Cl2 sccm | C T sec | Conv % | Sel % |
| 0.69 | 0.00 | 92.91 | 4.13 | 0.33 | 1.94% | 125 | 0.349 | 4.83 | 12.96 | 14 | 2.8 | 73.9 |
| 1.06 | 0.12 | 92.70 | 4.02 | 0.37 | 1.73% | 125 | 0.349 | 4.83 | 12.96 | 14 | 2.9 | 62.1 |
| 1.11 | 0.12 | 92.74 | 4.07 | 0.36 | 1.62% | 125 | 0.342 | 4.83 | 12.96 | 14 | 2.9 | 59.4 |
| 1.15 | 0.00 | 92.90 | 4.08 | 0.35 | 1.52% | 125 | 0.342 | 4.83 | 12.98 | 14 | 2.8 | 56.9 |
| 0.97 | 0.00 | 90.46 | 4.11 | 0.36 | 4.10% | 150 | 0.349 | 4.83 | 12.96 | 14 | 5.3 | 80.9 |
| 0.94 | 0.12 | 90.47 | 4.10 | 0.36 | 4.01% | 150 | 0.349 | 4.83 | 12.95 | 14 | 5.2 | 81.0 |
| 0.86 | 0.12 | 90.58 | 4.06 | 0.37 | 4.01% | 150 | 0.356 | 4.83 | 12.97 | 14 | 5.1 | 82.3 |
| 0.61 | 0.00 | 84.53 | 4.04 | 0.38 | 10.44% | 175 | 0.377 | 4.83 | 10.67 | 17 | 11.6 | 94.5 |
| 0.58 | 0.00 | 85.82 | 3.99 | 0.39 | 9.22% | 175 | 0.333 | 4.83 | 12.98 | 13 | 10.3 | 94.1 |
| 0.70 | 0.00 | 84.74 | 3.91 | 0.38 | 10.27% | 175 | 0.337 | 4.83 | 12.96 | 14 | 11.5 | 93.7 |
| 0.58 | 0.12 | 84.54 | 4.08 | 0.37 | 10.33% | 175 | 0.337 | 4.83 | 12.96 | 14 | 11.4 | 94.7 |
| 0.58 | 0.12 | 84.65 | 4.02 | 0.37 | 10.26% | 175 | 0.337 | 4.83 | 12.96 | 14 | 11.4 | 94.7 |
| 0.10 | 0.13 | 82.97 | 4.75 | 0.37 | 11.67% | 175 | 0.344 | 2.42 | 6.26 | 28 | 12.4 | 99.1 |
| 0.10 | 0.11 | 80.94 | 4.43 | 0.39 | 14.02% | 175 | 0.357 | 2.42 | 6.24 | 29 | 14.9 | 99.3 |
| 0.11 | 0.13 | 77.91 | 4.89 | 0.40 | 16.57% | 175 | 0.355 | 2.42 | 6.24 | 29 | 17.6 | 99.4 |
| 1.08 | 0.00 | 88.74 | 3.91 | 0.37 | 5.91% | 150 | 0.344 | 2.42 | 6.25 | 28 | 7.3 | 84.6 |
| 0.80 | 0.00 | 89.64 | 4.02 | 0.36 | 5.27% | 150 | 0.323 | 2.42 | 6.24 | 27 | 6.3 | 86.5 |
| 0.77 | 0.00 | 88.51 | 3.76 | 0.40 | 4.56% | 150 | 0.377 | 2.42 | 6.25 | 28 | 7.6 | 89.5 |
| 0.90 | 0.12 | 91.61 | 4.04 | 0.34 | 3.10% | 125 | 0.344 | 2.42 | 6.25 | 28 | 4.1 | 77.0 |
| 0.98 | 0.11 | 92.29 | 4.06 | 0.36 | 2.20% | 125 | 0.344 | 2.42 | 6.24 | 28 | 3.3 | 69.2 |
| 0.99 | 0.12 | 92.38 | 4.05 | 0.37 | 2.19% | 124 | 0.344 | 2.42 | 6.25 | 28 | 3.2 | 67.8 |

In Table 4, 236fa (HFC-1,1,1,3,3,3-hexafluoropropane) and 123 (HCFC-2,2-dichloro-1,1,1-trifluoroethane) are impurities in the feed to the reactor.

The reaction conditions provide a residence time of 27 to 29 seconds at a reactor temperature of 175° C., giving high selectivities in the production of HCFC-336mdd.

Example 10: Preparation of 2,3-dichloro-1,1,1,4,4,4-hexafluorobutane (HCFC-336mdd)

In this Example, the reaction is photoinitiated.

A 50 gallon (190 L) stirred reaction vessel equipped with a column, overhead condenser, dip-tube, and quartz light-well with a cooling jacket. The light-well fitted with a 450 watt mercury arc-lamp bulb.

To this reactor was charged 158 kg of E-1336mzz and this liquid was cooled to 0° C. The agitator on running a 100 rpm and the overhead condenser cooled to −−20° C. the light was turned on. To this system 69 kg of chlorine was slowly added through the dip-tube over 51 hours using the feed rate to control temperature and pressure. The liquid reaction temperature and pressure were not allowed to go above 10° C. and 1 psig (0.07 MPa), respectively.

On completion of the chlorine addition, the light was turned off and the solution was allowed to warm to room temperature. The system was vented to ambient through a caustic scrubber and the crude reaction mixture was de-inventoried to a storage vessel. Recovery of the HCFC-336mdd was carried out by combining 3 batches of the resulting crude reaction mixture (663 Kg/422 L) and then added slowly adding the crude reaction mixture through a dip-tube to a 200 gallon (750 L) stirred vessel equipped with bottom discharge valve and charges with 80 gallons (300 L) of an aqueous solution of 10% $K_2HPO_4/KH_2PO_4$. After the addition was done, this mixture was vigorously stirred for 3 hours and the agitation was then turned off. The lower organic phase was then decanted from the reactor using conductivity measurements to determine the change in phase. The resulting neutralized organic oil was a water-white liquid and had a pH of 5-6 was passed through a bed of molecular sieves to dry it and stored for final purification. Isolated chemical yield over 7 batches was 98%. The resulting GC assay (% FID) was 93.5% of the two 336mdd diastereomers (336mdd-dl and 336mdd-meso), the balance of the assay being heavy unknowns ~6% presumed to be oligomers of the product/starting materials, whereby the selectivity of the reaction was 93.5% Final purification was done by distillation.

Example 11. Preparation of 1,1,1,4,4,4,-hexafluoro-2-butyne

HCFC-336mdd was produced using the vapor phase process described under Example 9 in accordance with the specific information in Table 4 to provide selectivity of HCFC-336mdd of 99.4%.

NaOH aqueous solution (22 mL, 0.22 mole) was added to HCFC-336mdd (23.5 g, 0.1 mol) and water (5.6 mL) in the presence of Aliquat® 336 (0.53 g, 0.001325 mol), which is trioctylmethylammonium chloride, at room temperature. The reaction temperature was raised to 70° C. after the addition, and gas chromatography was used to monitor the reaction. The reaction was completed after 2 hour and 14 g 1,1,1,4,4,4,-hexafluoro-2-butyne product (conversion: 100%; yield: 86%) was collected in a dry ice trap. The butyne was purified by distillation.

Example 12: Preparation of Z-1,1,1,4,4,4-hexafluoro-2-butene 1,1,1,4,4,4-Hexafluoro-2-butyne produced according to Example 11 was reacted with hydrogen to produce the desired Z-isomer of 1,1,1,4,4,4-hexafluoro-2-butene by the following procedure: 5 g of Lindlar (5% Pd on $CaCO_3$ poisoned with lead) catalyst was charged to 1.3 L rocker bomb. 480 g (2.96 mole) of hexafluoro-2-butyne was charged in the rocker. The reactor was cooled (−78° C.) and evacuated. After the bomb was warmed to room temperature, $H_2$ was added slowly, by increments which did not exceed Δp=50 psi (0.35 MPa). A total of 3 moles $H_2$ were added to the reactor. A gas chromatographic analysis of the crude product indicated the mixture consisted of $CF_3C\equiv CCF_3$ (0.236%), trans-isomer E-$CF_3CH=CHCF_3$ (0.444%), saturated $CF_3CH_2CH_2CF_3$ (1.9%), $CF_2=CHCl$, impurity from starting butyne, (0.628%), cis-isomer Z—$CF_3CH=CHCF_3$ (96.748%).

Distillation of the crude product afforded 287 g (59% yield) of 100% pure cis-$CF_3CH=CHCF_3$ (boiling point 33.3° C.). MS: 164 [MI], 145 [M-19], 95 [$CF_3CH=CH$], 69 [$CF_3$]. NMR $^1H$: 6.12 ppm (multiplet), $^{19}F$: −60.9 ppm (triplet J=0.86 Hz). The selectivity of this reaction to the formation of the Z-isomer was 96.98%. The Z-isomer was recovered by distillation.

Other Embodiments

1. The present disclosure provides a process for producing Z-1,1,1,4,4,4-hexafluorobut-2-ene, comprising: (a) contacting 1,1,2,4,4-pentachlorobuta-1,3-diene with HF in the presence of a fluorination catalyst in the liquid phase to produce a product comprising 2-chloro-1,1,1,4,4,4-hexafluorobutane; (b) contacting 2-chloro-1,1,1,4,4,4-hexafluorobutane with base to produce a product comprising E-1,1,1,4,4,4-hexafluoro-2-butene; (c) contacting E-1,1,1,4,4,4-hexafluoro-2-butene with a chlorine source to produce a product comprising 2,3-dichloro-1,1,1,4,4,4-hexafluorobutane; (d) contacting 2,3-dichloro-1,1,1,4,4,4-hexafluorobutane with a base to produce a product mixture comprising 1,1,1,4,4,4-hexafluoro-2-butyne; and (e) contacting 1,1,1,4,4,4-hexafluoro-2-butyne with hydrogen to produce a product comprising Z-1,1,1,4,4,4-hexafluoro-2-butene.

2. The process of embodiment 1 may further comprise contacting trichloroethylene in the presence of a dimerization catalyst to produce a product mixture comprising 1,1,2,4,4-pentachlorobuta-1,3-diene.

3. The process of embodiment 1 may further comprise contacting trichloroethylene and pentachloroethane in the presence of a dimerization catalyst to produce a product mixture comprising 1,1,2,4,4-pentachlorobuta-1,3-diene.

4. The process of embodiment 2 or 3 may produce a product mixture comprising 1,1,2,4,4-pentachlorobuta-1,3-diene and trichloroethylene.

5. The process of embodiment 4 may further comprise recovering and recycling trichloroethylene to the process of embodiment 2.

6. The dimerization catalyst of any of embodiments 2-5 may comprise iron or copper.

7. The process of any of embodiments 2-6 may further comprise recovering 1,1,2,4,4-pentachlorobuta-1,3-diene from the product mixture and recycling the recovered 1,1,2,4,4-pentachlorobuta-1,3-diene to step (a).

8. In the process of any of embodiments 2-7, the dimerization catalyst comprises metallic iron.

9. In the process of any of embodiments 2-7, the dimerization catalyst comprises ferric chloride.

10. In the process of any of embodiments 2-7, the dimerization catalyst comprises metallic copper.

11. In the process of any of embodiments 2-7, the dimerization catalyst comprises cuprous chloride or cupric chloride.

12. In the process of any embodiment 3, the weight ratio of pentachlororethane to trichloroethylene is from about 0.001 to about 1 or from about 0.005 to about 1.

13. In the process of any of the preceding embodiments 1-12, the fluorination catalyst of step (a) is a Lewis acid catalyst.

14. In the process of any of the preceding embodiments 1-13, the molar ratio of HF to 1,1,2,4,4-pentachlorobuta-1,3-diene in step (a) is from about 1 to about 35.

15. In the process of any of the preceding embodiments 1-14, the product mixture of step (a) comprises 1,2-dichloro-1,1,4,4,4-pentachlorobutane.

16. In the process of any of the preceding embodiments 1-15, the base of step (b) is chosen from lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide.

17. In the process of any of the preceding embodiments 1-16, step (b) is performed in the presence of a phase transfer catalyst.

18. In the process of embodiment 17, the phase transfer catalyst is chosen from quaternary ammonium salt, heterocyclic ammonium salt, organic phosphonium salt, and non-ionic compound.

19. In the process of any of the preceding embodiments 1-18, step (c) is performed in the liquid phase.

20. In the process of any of the preceding embodiments 1-18, step (c) is performed in the vapor phase.

21. In the process of any of the preceding embodiments 1-20, the chlorine source in step (c) is chlorine.

22. In the process of any of the preceding embodiments 1-21, the base is a basic aqueous medium in step (d).

23. In the process of any of the preceding embodiments 1-22, step (d) is performed in the presence of a phase transfer catalyst.

24. In the process of any of the preceding embodiments 1-23, step (d) is performed in the presence of an alkali metal halide salt.

25. In the process of any of the preceding embodiments 1-24, the catalyst in step (e) is an alkyne-to-alkene catalyst.

26. In the process of embodiment 25, the alkyne-to-alkene catalyst is palladium catalyst dispersed on aluminum oxide or titanium silicate, doped with silver and/or a lanthanide.

27. In the process of embodiment 26, the palladium loading is from 100 ppm to 5000 ppm.

28. In the process of embodiment 26 or 27, the palladium catalyst is doped with at least one of silver, cerium or lanthanum.

29. In the process of embodiment 25, the alkyne-to-alkene catalyst is Lindlar catalyst.

30. In any of the preceding embodiments 1-29, the process further comprising recovering 2-chloro-1,1,1,4,4,4-hexafluorobutane from the product mixture of step (a) prior to step (b) or recovering E-1,1,1,4,4,4-hexafluoro-2-butene from the product mixture of step (b) prior to step (c) or recovering 2,3-dichloro-1,1,1,4,4,4-hexafluorobutane from the product mixture of step (c) prior to step (d) or recovering 1,1,1,4,4,4-hexafluoro-2-butyne hexafluorobutane from the product mixture of step (d) prior to step (e) or recovering Z-1,1,1,4,4,4-hexafluoro-2-butene from the product mixture of step (e).

31. The present disclosure provides a process for producing E-1,1,1,4,4,4-hexafluorobut-2-ene, comprising: (a) contacting 1,1,2,4,4-pentachlorobuta-1,3-diene with HF in the presence of a fluorination catalyst in the liquid phase to produce a product comprising 2-chloro-1,1,1,4,4,4-hexafluorobutane; and (b) contacting 2-chloro-1,1,1,4,4,4- hexafluorobutane with base to produce a product comprising E-1,1,1,4,4,4-hexafluoro-2-butene.

32. The present disclosure provides a process for producing Z-1,1,1,4,4,4-hexafluorobut-2-ene, comprising: (a) contacting 1,1,2,4,4-pentachlorobuta-1,3-diene with HF in the presence of a fluorination catalyst in the liquid phase to produce a product comprising 2-chloro-1,1,1,4,4,4-hexafluorobutane; and (b) contacting 2-chloro-1,1,1,4,4,4-hexafluorobutane with base to produce a product comprising E-1,1,1,4,4,4-hexafluoro-2-butene.

33. The process of embodiment 32 may further comprise contacting trichloroethylene in the presence of a dimerization catalyst to produce a product mixture comprising 1,1,2,4,4-pentachlorobuta-1,3-diene.

34. The process of embodiment 32 may further comprise contacting trichloroethylene and pentachloroethane in the presence of a dimerization catalyst to produce a product mixture comprising 1,1,2,4,4-pentachlorobuta-1,3-diene.

35. The process of embodiment 33 or 34 may produce a product mixture comprising 1,1,2,4,4-pentachlorobuta-1,3-diene and trichloroethylene.

36. The process of embodiment 35 may further comprise recovering and recycling trichloroethylene to the process of embodiment 2.

37. The dimerization catalyst of any of embodiments 33-36 may comprise iron or copper.

38. The process of any of embodiments 33-37 may further comprise recovering 1,1,2,4,4-pentachlorobuta-1,3-diene from the product mixture and recycling the recovered 1,1,2,4,4-pentachlorobuta-1,3-diene to step (a).

39. In the process of any of embodiments 33-38, the dimerization catalyst comprises metallic iron.

40. In the process of any of embodiments 33-38, the dimerization catalyst comprises ferric chloride.

41. In the process of any of embodiments 33-38, the dimerization catalyst comprises metallic copper.

42. In the process of any of embodiments 33-38, the dimerization catalyst comprises cuprous chloride or cupric chloride.

43. In the process of any embodiment 34, the weight ratio of pentachloroethane to trichloroethylene is from about 0.001 to about 1 or from about 0.005 to about 1.

44. In the process of any of the preceding embodiments 32-43, the fluorination catalyst of step (a) is a Lewis acid catalyst.

45. In the process of any of the preceding embodiments 32-44, the molar ratio of HF to 1,1,2,4,4-pentachlorobuta-1,3-diene in step (a) is from about 1 to about 35.

46. In the process of any of the preceding embodiments 32-45, the product mixture of step (a) comprises 1,2-dichloro-1,1,4,4,4-pentachlorobutane.

47. In the process of any of the preceding embodiments 32-46, the base of step (b) is chosen from lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide.

48. In the process of any of the preceding embodiments 32-47, step (b) is performed in the presence of a phase transfer catalyst.

49. In the process of embodiment 48, the phase transfer catalyst is chosen from quaternary ammonium salt, heterocyclic ammonium salt, organic phosphonium salt, and nonionic compound.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A process to produce Z-1,1,1,4,4,4-hexafluoro-2-butene comprising: (a') contacting trichloroethylene in the presence of a dimerization catalyst to produce a product mixture comprising 1,1,2,4,4-pentachlorobuta-1,3-diene (HCC-2320az), wherein the dimerization catalyst comprises iron or copper; (a) contacting 1,1,2,4,4-pentachlorobuta-1,3-diene produced in step (a') with hydrogen fluoride in the liquid phase in the presence of a fluorination catalyst to produce a product mixture comprising 2-chloro-1,1,1,4,4,4-hexafluorobutane (HCFC-346mdf); (b) contacting 2-chloro-1,1,1,4,4,4-hexafluorobutane with base to produce a product mixture comprising E-1,1,1,4,4,4-hexafluoro-2-butene (E-1336mzz); (c) contacting E-1,1,1,4,4,4-hexafluoro-2-butene with a chlorine source in the presence of a catalyst to produce a product mixture comprising 2,3-dichloro-1,1,1,4,4-hexafluorobutane (HCFC-336mdd); (d) contacting 2,3-dichloro-1,1,1,4,4,4-hexafluorobutane with a base to produce a product mixture comprising 1,1,1,4,4,4-hexafluoro-2-butyne; and (e) contacting 1,1,1,4,4,4-hexafluoro-2-butyne with hydrogen to produce a product mixture comprising Z-1,1,1,4,4,4-hexafluoro-2-butene, wherein step (a') is performed in the presence of pentachloroethane, wherein the weight ratio of pentachlororethane to trichloroethylene is from about 0.001 to about 1.

2. The process of claim 1, wherein the catalyst in step (a) is a metal halide.

3. The process of claim 1, wherein steps (b) and (d) are performed in the presence of a phase transfer catalyst.

4. The process of claim 1, wherein step (c) is performed in the presence of a vapor phase catalyst in the vapor phase.

5. The process of claim 1, wherein step (c) is performed in the presence of a liquid phase catalyst in the liquid phase.

6. The process of claim 1, wherein step (c) is performed with photoinitiation.

7. The process of claim 1, wherein step (e) is performed in the presence of an alkyne-to-alkene catalyst, comprising palladium.

8. The process of claim 1, further comprising recovering 2-chloro-1,1,1,4,4,4-hexafluorobutane from step (a).

9. The process of claim 1, further comprising recovering E-1,1,1,4,4,4-hexafluoro-2-butene from step (b).

10. The process of claim 1, further comprising recovering 2,3-dichloro-1,1,1,4,4,4-hexafluorobutane from step (c).

11. The process of claim 1, further comprising recovering 1,1,1,4,4,4-hexafluoro-2-butyne from step (d).

12. The process of claim 1, wherein the temperature of step (a') is greater than 200° C. and less than 245° C.

13. The process of claim 1, wherein, following step (a'), the pentachlororethane is recovered and recycled.

* * * * *